United States Patent [19]

Houston et al.

[11] Patent Number: 5,024,834
[45] Date of Patent: Jun. 18, 1991

[54] THIOETHER LINKED IMMUNOTOXIN CONJUGATES

[75] Inventors: L. L. Houston, Oakland; Lois Aldwin, San Mateo; Danute E. Nitecki, Berkeley, all of Calif.

[73] Assignee: Cetus Corporation, Emeryville, Calif.

[21] Appl. No.: 597,081

[22] Filed: Oct. 15, 1990

Related U.S. Application Data

[62] Division of Ser. No. 217,938, Jul. 12, 1988, abandoned.

[51] Int. Cl.$^5$ .................. A61K 39/44; C07K 17/02
[52] U.S. Cl. ........................ 424/85.91; 424/85.8; 530/388; 530/389; 530/390; 530/391
[58] Field of Search ................. 424/85.8, 85.91; 530/390, 391, 389, 388

[56] References Cited

U.S. PATENT DOCUMENTS

| | | | |
|---|---|---|---|
| 4,762,707 | 8/1988 | Jansen et al. | 424/85.91 |
| 4,943,636 | 7/1990 | Nitecki et al. | 546/294 |
| 4,981,979 | 1/1991 | Sivam | 548/545 |

FOREIGN PATENT DOCUMENTS

| | | |
|---|---|---|
| 226418 | 6/1987 | European Pat. Off. . |
| 306943 | 3/1989 | European Pat. Off. . |

OTHER PUBLICATIONS

Blair et al. (1983) J. Immunol Methods 59, 129-143.
Ghose et al., (1983) Methods Enzymol 93: 280-333.
Vallera et al., (1983) Science 222: 512-515.

Primary Examiner—Jeffrey E. Russel
Assistant Examiner—Kay Kim
Attorney, Agent, or Firm—Gregory J. Giotta; Albert P. Halluin

[57] ABSTRACT

Heterobifunctional crosslinkers up to about 34 Å in length consisting of a sulfhydryl reactive group linked to a spacer group, which in turn is linked to an activated carboxylate group, that are useful for making efficacious anticancer immunotoxin conjugates as shown preferably by reacting an antibody associated amino group with the activated carboxylate group to form an antibody crosslinker complex and reacting the antibody crosslinker complex with a cytotoxin having a reactive sulfhydryl group with the sulfhydryl reactive group of the crosslinker, and using the conjugates so produced to treat cancer patients.

5 Claims, 2 Drawing Sheets

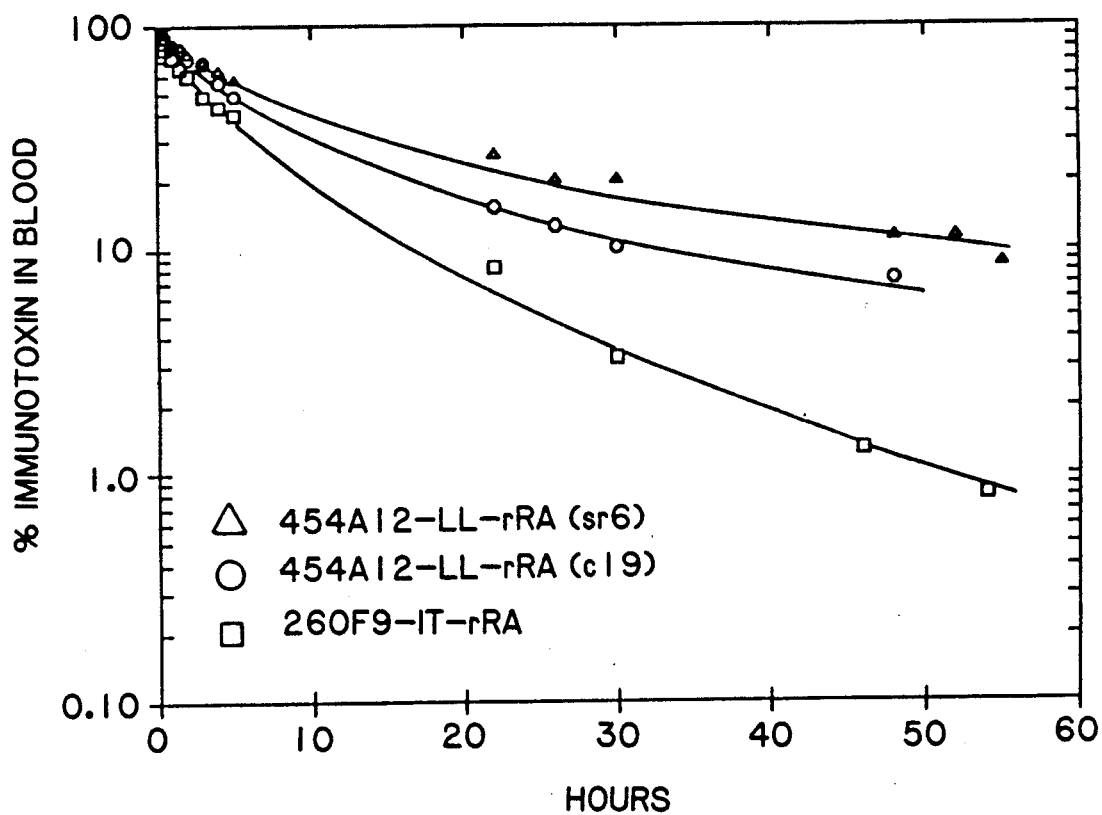

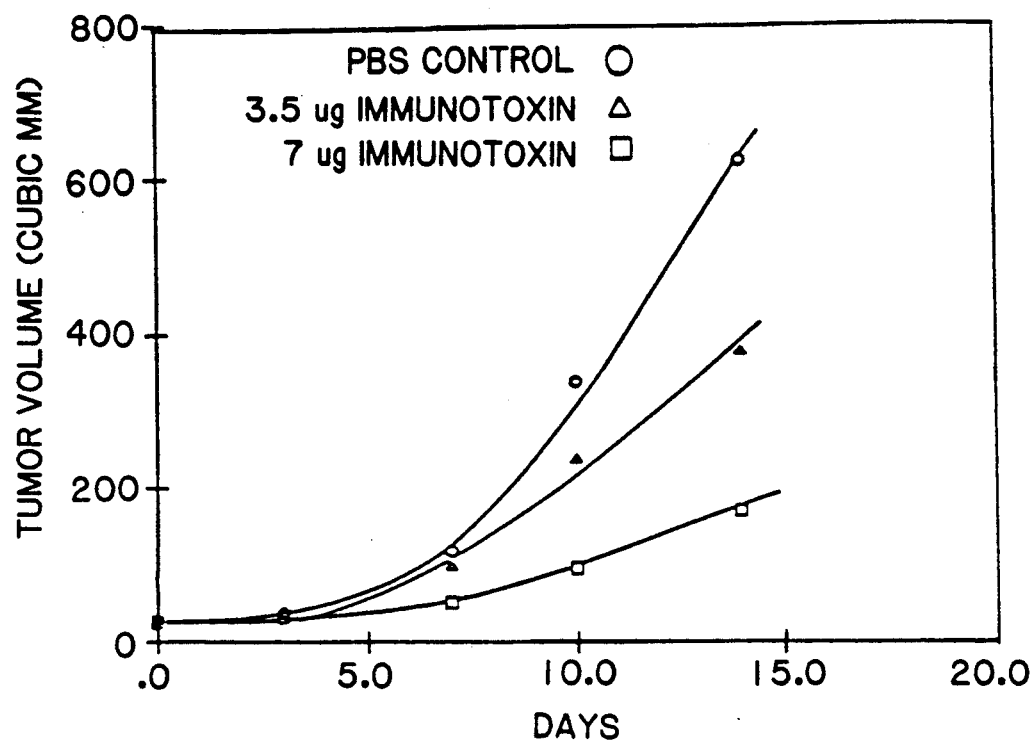
FIG. 2 260F9-LL-rRA ON MX-1 TUMOR
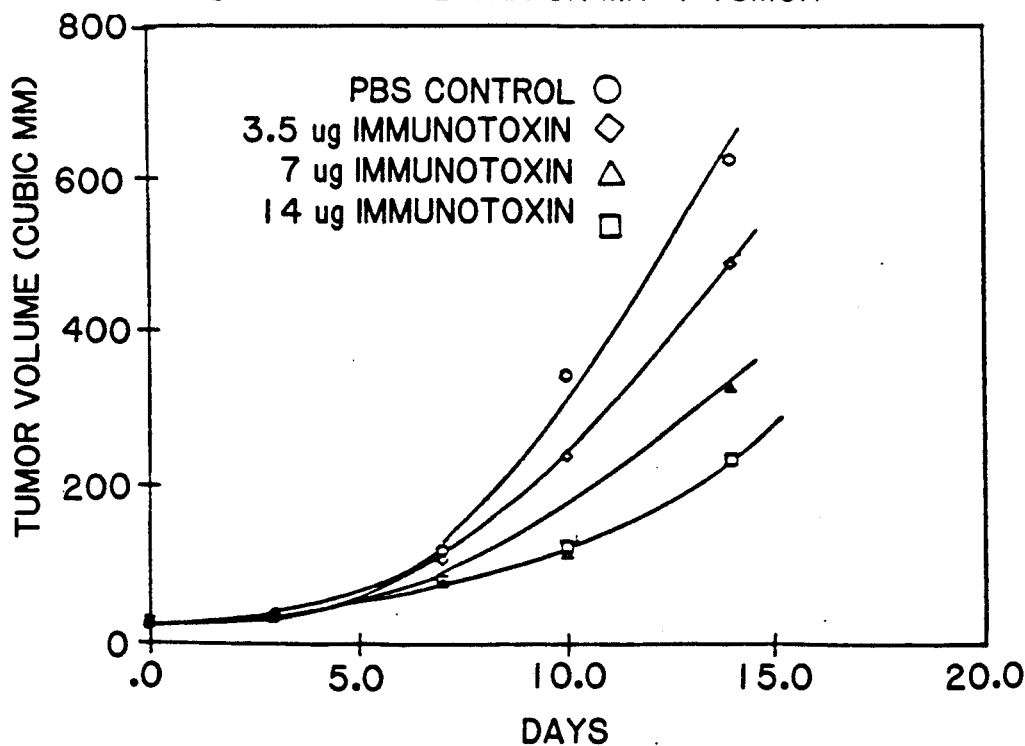
FIG. 3 260F9-LL-rRA ON MX-1 TUMOR

THIOETHER LINKED IMMUNOTOXIN CONJUGATES

This application is a division of application Ser. No. 217,938, now abandoned filed 7-12-88.

FIELD OF THE INVENTION

This invention is in the area of molecular pharmacology and illustrates immunotoxin conjugates, and methods of making the same, that are useful in treating various diseases, including cancer, consisting of antibody and a cytotoxic moiety linked by a thioether covalent bond.

BACKGROUND OF THE INVENTION

In the past few years there has been the development of numerous "immunotoxins" which consist of a cell type specific targeting antibody linked to a cytotoxic agent. The antibody generally recognizes a plasma membrane antigen to which the immunotoxin binds. After the immunotoxin is bound to the cell surface, it is endocytosed into the cell, where it interferes with cellular biochemical reactions, generally protein synthesis, thereby causing cell death. Thus, immunotoxins have three key components, the cell targeting antibody molecule, the covalent bond which holds antibody and toxin together, and the cytotoxic agent. Vitetta et al. *Science*, 238:1098 (1987).

Most often the antibody portion of an immunotoxin consists of a monoclonal antibody. Kohler and Milstein, *Nature* (London) 256:495 (1975). Monoclonal antibodies are chemically homogenous, and thus facilitate the construction of truly cell type specific immunotoxins. Immunotoxins can, however, be constructed with polyclonal antibodies.

A variety of molecules have been used for the toxin portion of the conjugate, including alkylating and anoimetabolic agents, as well as alkaloids and various toxic proteins or peptides and portions or fragments of toxins. The latter molecules (toxins) are generally produced by bacteria or plants and exert their cytoxic effect by enzymatically interrupting protein synthesis at the ribosomal level. Enzymatically active toxin and fragments thereof are often preferred, and are exemplied by diphtheria A chain, non-binding active fragments of diphtheria toxin, exotoxin A chain (*Pseudomonas aeruginosa*), abrin A chain, and ricin A chain.

Binding of antibody to the toxin is effected by a covalent linkage, the nature of which varies depending on the type of toxin employed. For protein or peptide toxins, generally disulfide bond is used to link antibody to the toxin. This type of linkage has been widely used because it is generally believed that the cytotoxic moiety must be released from the antibody after entry into the cell for the toxin to exert its effect. A disulfide link between antibody and toxin is served by the reducing environment inside the cell. Examples of reagents that have been used to from the disulfide bond include N-succinimidyl-3-(2-pyridyl- dithio(propionate) (SPDP), and 2-iminothiolane hydrochloride (2-IT).

One of the drawbacks associated with the use of a disulfide bond is that the bond is cleaved in the extra cellular circulation. Blakey et al. *Cancer Research*, 47:947 (1987); Levin et al., *J. Clin. Invest.*, 77:977 (1986). For example, it has been shown that a significant fraction of immunotoxin is cleaved in the blood within eight hours of intravenous administration, and most of the conjugate is cleaved within 24 hours. Thus, the amount of immunotoxin available for reaction with the target cell is not as great as may be desirable, and, moreover, free antibody may compete with the immunotoxin for binding to the target cell thus reducing the efficacy of treatment. In addition, toxicity and other pharmacological preparation may be effected by the release of the toxin moiety.

Several patents show chemicals that have been, and continue to be utilized for forming disulfide cross-linked immunotoxins. U.S. Pat. Nos. 4,350,626 and 4,450,154 claim immunotoxins in which a monovalent (Fab), or divalent (Fab'), fragment of antibody having tumor cell type specificity is coupled to recin A chain. Coupling was affected through cysteine-thiols on the two proteins, with or without an intervening bifunctional cross-linking group. Moreover, U.S. Pat. Nos. 4,357,273 and 4,638,049 describe similar immunotoxins wherein diphtheria toxin was conjugated in lieu of ricin A chain. U.S. Pat. No. 4,534,211 discloses conjugates wherein the cytotoxic moiety is attached to the antibody by at least one sulphur atom. Lastly, U.S. Pat. No. 4,340,535 shows antibody-ricin A conjugates wherein the disulfide bond is effected by SPDP.

In addition to disulfide bonds, antibody and toxins have also been joined by other chemical bonds. One construct makes use of an acid-labile crosslink. The acid-labile linkage is served when the conjugate is taken up by a cell and compartmentalized into a cellular compartment having a pH value which is lower than that outside the cell. Blatter et al., *BioChem.*, 24:1517 (1985). A second means of crosslinking antibody and toxin has been to use a peptide bond with an amino acid sequence that is thought to be recognized by proteases found in the cell's cytoplasm. U.S. Pat. No. 4,571,958. Neither of these crosslinkers are favored in constructing immunotoxins as either they breakdown more rapidly than the disulfide bond crosslinkers in blood, or else the linkage is not readily served once the conjugate has entered the cytoplasm.

Finally, there have been several reports wherein antibody and cytotoxin are linked by a thioether covalent bond. Wawrzynczak E., and Thorpe, P. (1987), Methods for Preparing Immunotoxins: Effect of the Linkage on Activity and Stability. In Immunoconjugates, Antibody Conjugates in Radioimaging and Therapy of Cancer (C-W., Vogel, ed), New York, Oxford University Press, pp. 28-55. These conjugates were developed to obviate the undesirable cleavage of antibody and toxin which occurs in the extra cellular circulation associated with disulfide linked conjugates. Thioether linked immunotoxins are, however, considerably less active than disulfide linked immunotoxins. For example, thioether conjugates exhibit 70% less protein synthesis inhibitory activity in vitro assays, and are 99% less cytotoxic compared to analogous disulfide conjugates. The loss of efficacy is throught to result, at least in part, from the inability of toxin to separate from antibody once the conjugate is taken up inside the cell, a putative requirement for cytotoxicity. For example, it has been stated by Fulton et al., that "If the bond between antibody and A chain is not reducible, then toxicity is virtually abolished", Fulton, R. et al., (1987), Immunotoxins containing ricin A and B chains: In Immunoconjugates, Antibody Conjugates in Radioimaging and Therapy of Cancer (C. W. Vogel, ed), New York, Oxford University Press, pp. 56-70. Consequently, despite their extra cellular stability thioether bonds are disfavored to form immunotoxin conjugates.

It should be apparent from the foregoing discussion that the preferred linkage between antibody and toxin should be stable in the extra cellular circulation, and highly cytotoxic after it is endocytosed by the target cell.

SUMMARY OF THE INVENTION

Accordingly, the present invention described herein shows highly efficacious immunotoxin conjugates wherein antibody and cytotoxin are linked by novel nonlabile thioether bonds.

A second object of the invention is to provide a description of heterobifunctional crosslinkers for linking antibody and cytotoxin to form immunotoxins wherein antibody and cytotoxin are linked by a linker containing thioether bond. The linker has extended chain length up to about 34 Å.

A further object of the instant invention is to provide immunotoxins consisting of the cytotoxin recombinant ricin A chain and antibody linked by a thioether bond that are efficacious in cancer therapy.

A yet additional object of the invention is to provide a description of a class of heterobifunctional crosslinkers suitable for linking antibody and cytotoxin via thioether bond to form immunotoxins consisting of an activated carboxylate, a long spacer containing ether group, and a maleimido group.

BRIEF DESCRIPTION OF THE DRAWINGS

Table 1 shows the effect of immunotoxins on protein synthesis and mitochondrial reductase activity.

FIG. 1 reveals a biphasic clearance of immunotoxin from blood.

FIGS. 2 and 3 compare the effect of immunotoxin conjugates in the MX-1 tumor system linked via mal-sac-sp-glut-HNSA or iminothiolane consisting of 260F9 monoclonal antibody and recombinant ricin A chain.

DETAILED DESCRIPTION OF THE INVENTION

The instant invention presents immunotoxin conjugates consisting of antibody and a cytotoxic agent linked by a thioether bond formed by reacting these molecules with a heterobifunctional maleimide-active ester crosslinker. To facilitate understanding the invention certain terms used herein are defined below.

Toxin or cytotoxins as defined herein have the same meaning and include virtually all cytotoxic agents having a reactive sulfhydryl or amino group. Exemplary cytotoxins include proteins (i.e. tumor necrosis factor, TNF) small molecular weight anti-cancer drugs, or enzymatically active molecules of bacterial or plant origin, or an enzymatically active fragment (i.e. A chain) derived therefrom. All are meant to come within the scope of this definition. Enzymatically active toxins and fragments thereof are preferred and are exemplified by diphtheria A chain, non-binding active fragments of diphtheria toxin, exotoxin A chain (*Pseudomonas aeruginosa*), recin A chain, abrin A chain, saporin, modeccin A chain, alpha-saccarin, Aleurites fordii proteins, dianthin proteins, *Phytolacca americana* proteins (PAP I, PAP II, and PAP-S), among others. Ricin A chain, non-binding active fragments of diphtheria toxin, abrin A chain, various species of PAP, and saporin are most preferred. The sulfhydryl or amino groups associated with the toxin can be a part of the natural structure of the toxin, or incorporated by reaction with chemicals that do not affect, or minimally affect, its cytotoxic activity.

The term antibody is well understood in the art and its meaning is similarly applicable here. Encompassed within this definition are fragments of antibody that retain antigen binding activity. Antibody fragments include the Fab, Fab', Fv, and F(ab')2 regions, or derivatives or combinations thereof. The derivation of these antibody fragments by enzymatic digestion of polyclonal or monoclonal antibody is well known to those skilled in the art. It will be further appreciated that emcompassed within the definition of antibody is single chain antibody that can be generated as described in U.S. Pat. No. 4,704,692, as well as hybrid antibodies described by Monroe, Nature, 312:779, Morrison, Science, 229:1202 (1985), and Oi et al., *BioTechniques*, 4:214 (1986). Particularly useful are hybrid or "humanized" antibodies made as described in European Patent Application No. 302,620. These publications, as well as others described herein, are hereby incorporated by reference in their entirety.

Immunotoxin conjugate is defined to mean an immunotoxin having antibody and toxin joined by a covalent linkage. The number of antibody and cytotoxic molecules bound thereto may vary per immunoconjugate complex.

Heterobifunctional crosslinkers, also termed maleimide active esters, referred to herein encompass a family of crosslinkers that produce a thioether bond linking antibody and toxin consisting of an activated carboxylate, a spacer molecule that contains ether groups, and a maleimido group to which a thiol on the cytotoxin can bind. The linker will have a preferred extend chain length of up to about 34 Å angstroms; however, longer linkers are intended to come within the scope of the invention.

Synthesis of Heterobifunctional Crosslinkers

The thioether bond that links antibody and toxin described herein result from heterobifunctional crosslinkers having two reactive groups, an active ester designed to react primarily with amino groups, preferably on the antibody molecule; and a maleimido group that reacts with sulfhydryl groups, preferably present on the cytotoxin. It is important to note, however, that by suitable chemical modification of antibody or cytotoxin that reaction of antibody can be made to occur with the maleimido group, and reaction of cytotoxin with the active ester. For example, antibody or antibody fragments can be prepared having free sulfhydryl groups by techniques well known in the art. Particularly useful is the procedure shown in U.S. Pat. No. 4,698,420 which is hereby incorporated by reference. Certain classes of antibody, specifically IgM and IgA, exist as aggregates such that antibody molecules are joined together by disulfide bonds. Reduction of the aggregates causes the formation of individual antibody molecules having free sulfhydryl groups which can be reacted with the maleimido group of the instant heterobifunctional crosslinkers. Similarly, antibody fragments can be produced using suitable enzymes, and reduced thereby rendering sulfhydryl groups available for reaction.

Alternatively, in lieu of reducing antibody or antibody fragments to obtain a reactive sulfhydryl group, sulfhydryl group(s) can be introduced into these molecules by reactions described in U.S. Pat. Nos. 4,350,626, 4,450,154, and 4,340,535, which are hereby incorporated by reference. Regardless of how the sulfhydryl group is realized, antibody, or antibody fragment, is reacted with the heterobifunctional crosslinker at pH's which favor sulfhydryl maleimide reaction, preferably about pH 6.

The heterobifunctional crosslinkers of the present invention consist of an activated carboxylate, a spacer containing ether groups, and a maleimido group. The initial step in the synthesis of this type of crosslinker consists of employing an ether containing spacer group, preferably an ether diamine, having amino reactive groups on both ends of the spacer, with a reversible amino protective reactive group to block one of the amino groups. Next, the remaining amino group is reacted with a dicarboxylic anhydride; glutaric anhydride and succinic anhydride can be employed, among others. The protecting group is then removed, preferably by exposure to acid, and the deprotected amino group reacted with an active ester containing maleimido group to introduce a maleimide functionality at this region of the spacer. At this point in the synthesis the spacer contains a maleimido group at one end, and a group capable of forming an active ester, that is to say, a carboxylic acid, at the other. This molecule is then reacted with 1-hydroxy-2-nitrobenzene-4-sulfonic acid in the presence of a suitable condensing agent to yield the maleimide containing active ester. It will, of course, be understood by those skilled in the art that each of the reactions described above is followed by suitable purification procedures.

It is important to note that spacers of various length can be employed to produce the instant crosslinkers. The preferred spacer has a length of about 34 Å; however, additional spacers considerably shorter or longer in length can be used and are available from Texaco Chemical Company under the trade name Jeffamine.

In more detail, the synthesis of the heterobifunctional crosslinkers involves initially reacting the diamino containing spacer with the protecting group, 2-tert-butoxycarbonyloxyimino-2-phenyl-acetonitrile, (BOC-ON). Suitable chromatographic techniques permit the isolation of the mono-BOC-spacer NH2 molecule. The preferred dicarboxylic anhydride, glutaric anhydride, is reacted with the mono-BOC-spacer amine. Suitable chromatographic isolation of the reactants yields BOC-spacer-glutarate. The BOC group is removed, generally using trifluoroacetic acid, the acid removed and the product reacted with a suitable active maleimido ester, preferably maleimido-6-aminocaproyl- ester of 1- hydroxy-2-nitrobenzene sulfonic acid, to yield maleimido-6-aminocaproyl-spacer-glutarate, that hereafter is abbreviated mal-sac-spacer-glut. Finally, the heterobifunctional crosslinker is produced by reacting 1-hydroxyl-2-nitrobenzene 4-sulfonic acid with mal-sac-spacer-glut in the presence of a suitable condensing agent, such as dicyclohexylcarbodiimide. Thus, the preferred heterobifunctional maleimide-active ester crosslinker is maleimido-6-aminocaproyl-spacer-glutarate ester of 1-hydroxyl-2-nitrobenzene-4-sulfonic acid, abbreviated as mal-sac-spacer-glut-HNSA.

Synthesis of Immunoconjugates Containing a Thioether Bond

In general, the procedure for forming the immunotoxin conjugate consist of reacting antibody, either polyclonal or monoclonal, having a free amino group with a maleimide-active ester crosslinker, produced as described above, in a suitably buffred solution. Preferably, the maleimide-active ester is present in about a two-fold molar excess over antibody, and the pH of the solution is slightly alkaline to maintain some of the antibody's amino group in an unprotonated state. The reaction of antibody with the crosslinker can be followed by monitoring the absorbance of the solution at a wavelength of about 406 nm. Aldwin and Nitecki *Analytical Biochemistry*, 164:494 (1987). An increase in absorbance at this wavelength is the result of the dianion leaving group, HNSA, and the reaction of antibody amines to form stable amide bonds. Because hydrolysis of the crosslinker's active ester is slow relative to aminolysis most of the leaving groups absorbance is due to amide bond formation. The reaction of antibody with the crosslinker is for a time sufficient to introduce about 0.5–3 crosslinker molecules per antibody molecule. Next, the derivatized antibody is separated from the crosslinker, using any number of standard biochemical separation techniques. Preferably the separation procedure will be accomplished using a gel filtration column, and more preferably Sephadex G-25 (Pharmacia Corp.) will be employed. The column is preequilibrated with a chromatographically compatible aqueous buffered solution. The isolated derivatized antibody can then be reacted with a toxin as described below.

Cytotoxins having a free sulfhydryl group can be directly reacted with the derivatized antibody in an aqueous buffered solution compatible with the reaction. If the cytotoxin does not have a free sulfhydryl group, but does not disulfide bonds, the cytotoxin is reduced with an appropriate reducing agent to produce reactive sulfhydryl groups. Alternatively, the cytotoxin may be thiolated using techniques well known in the art. In either instance, reducing agents are separated from the cytotoxin by techniques also well known to those skilled in the art, including dialysis or gel exclusion chromatography, and then reacted with the derivatized antibody. The cytotoxin and antibody concentrations, and the duration of the reaction may vary depending on the number of toxin sought to be bound to antibody. Generally, the preferred ratio of cytotoxin::antibody is 1:1; and the reaction is run at 4° C. overnight.

Purification of the crude immunotoxin conjugate mixture may be realized using various biochemical materials and methods, such as ion exchange chromatography, high pressure liquid chromatography, hydrophobic chromatography, and size exclusion chromatography. The preferred purification technique of the instant invention is hydrophobic interaction chromatography and is carried out as follows. The conjugate mixture as prepared above its first loaded on to a sizing column to remove unreacted cytotoxin and any high molecular weight aggregates present in the reaction mixture. This step is readily achieved using the preferred chromatographic column, Sephacryl S-300 (Pharmacia Corp.). The column is equilibrated in a suitable aqueous salt solution having a pH in the range of about 6–7. The eluate from the sephacryl S-300 column is then chromatographed over a hydrophobic interaction column, such as phenylsepharose CL-4B (Phrmacia Corp.) or TSK phenyl-5PW Toyo Soda Kogyo K.K. This chromatographic step can be effected in the same buffer used to carry out the Sephacryl S-300 step, but in addition containing an elevated amount of salt, preferably about 1 M. Moreover, when the phenylsepharose hydrophobic column is employed, the buffer used in both the sizing chromatographic step and the subsequent chromatographic separation step will preferably contain sodium chloride as the salt. In contrast, when TSK phenyl-5 PW is employed, ammonium sulfate is the preferred salt. The immunotoxin and unreacted antibody are eluted from the column by gradually decreasing with each column volme the amount of salt. Generally about 4–7 column volumes will be sufficient. Additionally, immunoconjugate and antibody can be eluted in an aqueous salt solution having a reduced amount of salt, but containing a chaotropic agent, preferably a polyol, and more preferably propylene glycol, but other agents are also suitable including glycerol and ethanol. If propylene glycol is employed, free antibodyis eluted first, followed by various "mers", that is to say immunoconjugates containing one or more cytotoxins bound to antibody. Generally a "1-mer" is eluted first, a "2-mer" is eluted second, and so forth.

Fractions containing either free antibody or immunoconjugate can be identified using a suitable analytical technique, such as sodium dodecylsulfate polyacrylamide gel electrophoresis. The immunotoxin conjugates so isolated can, if desired, be concentrated by any suitable technique known in the art followed by sterilization. The latter is readily achieved by passing the immunotoxin conjugate through an 0.2 micron fiber.

An alternative method of separating immunotoxin conjugates from free antibody is to employ a "fast flow" chromatographic separation and purification step using a hydrophobic gel. Gel material that can be used include either phenylsepharose or TSK phenyl-5 PW, among others. Phenlsepharose is preferred wherein the matrix material contains half the number of phenol groups normally present. This type of gel is less hydrophobic, and thus does not bind the immunotoxin conjugate or free antibody quite as strongly. In this format free antibody is removed with the initial column volume of low salt solution, as described above, and the immunotoxin conjugate is typically removed in a second column volume of buffer containing between about 10%–60% of a chaotropic agent, preferably propylene glycol. This procedure is characterized in that the concentration of salt, preferably sodium chloride or ammonium sulfate in the first column volume of an eluant depending on the modified gel selected as above, is about 1.5 molar. The procedure realizes eluted immunotoxin conjugate in a relatively concentrated form, about 4 mg/ml, thereby obviating further concentration of the immunotoxin conjugate.

Having generally described the invention, examples of particular applications of the invention will be presented below. However, it will be understood by those skilled in the art that the examples are presented in the spirit of illustration, and are not intended to limit the scope of the invention.

EXAMPLE I

Synthesis of
Maleimido-6-Aminocaproyl-NH-(CH2)3-O-(CH2)4-O-(CH2)3-NH-Glutary Ester of
1-Hydroxyl-2-Nitrobenzene Sulfonic Acid A maleimido active ester crosslinker about 34 Å in length, as measured from the two reactive functional groups of the spacer, was synthesized as follows. Approximately 61.4 grams of the ether diamine, 4,9-dioza-1,12-dodecanediamine, was dissolved in 600 ml of anhydrous methanol. To this solution was added a slurry containing 81.2 grams of 2- (tert-butoxycarbonyloxyimino)-2-phenylacetonitrile (BOC-ON) in 150 ml methanol. The latter is an amino group protective agent. The mixture was allowed to react overnight, and then concentrated by rotary evaporation, followed by purification on a silica gel column. The mixture was added to the column, and the column first exposed to chloroform:methanol:acetic acid, 80:20:10. This solvent removed the bis-BOC of the 4,9-dioxa-1,12-dodecanediamine derivative, and the mono-BOC dodecanediamine derivative was eluted with chloroform:methanol:acetic acid, 70:30:5. Approximately 53.1 grams of a thick oil was produced, and thin layer chromatography using chloroform:acetic acid, 90:10 revealed the starting material, 4,9-dioxa-1,12-dodecanediamine to have a $R_f$ value of about 0.08, which was visualized with iodine vapor or ninhydrin. The mono- BOC protected 4,9dioxa-1,12 dodecanediamine had a $R_f$ of about 0.72 and also was reactive with iodine vapor or ninhydrin. High voltage paper electrophoresis having a pH 1.85, and run at 5000 volts for 20 minutes revealed that the diamine starting material had a migration distance of 8.8 centimeters and the mono-BOC derivative had a migration distance of about 4.7 centimeters. At a pH 3.5, the diamine starting material migrated 14.4 centimeters and the mono-BOC protected diamine had a migration distance of about 6.1 centimeter.

The mono protected spacer (BOC-spacer-NH2) was derivatized to contain an acid reactive group by adding 4.1 grams of BOC-spacer-NH2 in 40 ml of pyridine, followed by the addition of a two fold molar excess, or 3.08 grams of glutaric anhydride. The reaction was allowed to proceed overnight, followed by removal of the pyridine in vacuo. The residue was taken up in chloroform and extracted three times with 0.5M aqueous citric acid, followed by three further extractions with saturated, aqueous sodium chloride. The chloroform phase was dried over anhydrous magnesium sulfate and concentrated to a thick oil by rotary evaporation. This resulted in crude BOC-spacer-glutarate (BOC-spacer-glut), which was purified on a silicate gel column in a solvent system comprising chloroform: acetic acid, 90:10. About 1.48 grams of a thick oil was recovered, and thin layer chromatography using a developing solvent of methyl-t-butyl ether: chloroform: acetic acid, 6:3:1, revealed an iodine and ninhydrin positive species with an $R_f$ of about 0.14, and a second species with an $R_f$ of about 0.49, which also rected with iodine, but did not react with ninhydrin. The iodine/ninhydrin reactivity profile indicated that the species with the $R_f$ value of 0.14 is BOC-spacer-NH$_2$, which would be expected to react with both reagents. Ninhydrin reacts with the free amino group. In contrast, the absence of ninhydrin staining with the species having the $R_f$ value of 0.49 is consistent with the formation of BOC-spacer-glut. This was supported by the observation that when the protecting group, BOC, was removed with 6 NHCl, the resulting deprotected molecule was ninhydrin positive.

Further characterization of the reaction protect revealed that in n-butanol:acetic acid:water, 120:30:50, BOC-spacer-NH$_2$ had an $R_f$ of about 0.73 and the BOC-spacer-glut an $R_f$ of about 0.83.

BOC-spacer-glut was treated with trifluoroacetic acid to remove the BOC group. This was carried out by dissolving 1.6 grams of BOC- spacer-glut-OH in 20 ml of 95% trifluoroacetic acid followed by stirring for 30 minutes at room temperature. Trifluoroacetic acid was removed by rotary evaporation, and the residual oil dried overnight in vacuo. The resulting deprotected, NH$_2$- spacer-glut was dissolved in 2.0 ml of dimethylformamide. This solution was neutralized with diisopropylethylamine, followed by adding 2.68 grams of maleimido-6- aminocaproyl ester of 1-hydroxy2-nitrobenzene-4-sulfonic acid (sodium salt). The reaction was effected at room temperature with continuous stirring. The progress of the reaction was monitored by measuring the formation of the amount of 1-hydorxy-2-nitrobenzene sulfonic acid dianion that results from the aminolysis of the active ester. This is readily achieved by diluting 1 microliter aliquotes of the reaction mixture into 5 ml of 0.01M phosphate buffer, pH 7.0 and reading the absorption of the solution at 406 nm in a spectrophotometer. A method for performing this procedure is described adequately by Aldwin and Nitecki, above.

After the reaction had gone to completion, generally within about thirty minutes, the mixture was chromatographically purified on a LH-20 Sephadex column (4.5 cm×40 cm preequilibrated in dimethylformamide). Maleimido-6-aminocaproyl-spacer-glutarate (mal-sac-spacer-glut) eluted first from the column. Fractions containing this derivative were pooled, concentrated in vacuo and purified using preparative thin layer Chromatotron chromatography. Four mm thick silicate gel plates were employed with the solvent chloroform-:methanol:acetic acid, 90:10:10. A further purification was achieved using high pressure liquid chromatography with a Waters DeltaPrep 3000 HPLC on a microBondapak C18 column and a gradient of acetonitrile in 0.1% aqueous trifluoroacetic acid. About 0.3 grams of product was obtained. Thin layer chromatography using chloroform, acetic acid, methanol, 90:10:10 revealed that mal-sac- spacer-glut had an R$_f$ of about 0.66, whereas in the solvent system chloroform:methanol:acetic acid, 70:3:5 an R$_f$ of about 0.92 was observed. Consistent with the formation of mal-sac-spacer-glut was the reaction of the product with iodine vapor, chlorox spray, which is indicative of amide bonds, and a reagent reactive with maleimides, Keller, O. and Rudinger, J., Helv. Chim. Acta, 58:531 (1975).

Lastly, meleimido-6-aminocaproyl-spacer-glutaryl ester of 1- hydroxy-2-nitrobenzene sulfonic acid was formed by dissolving 0.2 grams of mal-sac-spacer-glut-OH in 4.0 ml of dimethylformamide, followed by adding 0.534 grams of 1-hydroxy-2-nitrobenzene sulfonic acid and 0.305 grams of dicyclohexylcarbodiimide. The mixture was allowed to react overnight at room temperature, and the active ester product chromatographed over a LH-20 Sephadex column as described above. The identification of fractions containing mal-sac-spacer-glut-HNSA was achieved by spotting a drop of a fraction on to a porcelain plate, followed by the addition of a drop of 5N NaOH. The latter causes the hydrolysis of the ester, thereby producing a bright yellow color indicative of the HNSA anion. Fractions so identified as to contain mal- sac-spacer-glut-HNSA had the dimethylformamide removed in vacuo, and purified on a silica gel Chromatotron 2 mm thick thin-layer-chromatographic plate, using a solvent system consisting of chloroform:methanol:acetic 70:30:5. The ester containing fractions identified as described previously were pooled and concentrated by rotary evaporation. About 0.113 grams of a pale yellow solid product was obtained which contained 94.1% ester. The product was shown to have a R$_f$ of about 0.25 in chloroform:acetic acid:methanol, 90:10:10, and an R$_f$ value of about 0.75 in chloroform:methanol:acetic acid, 70:30:5. Spectral analysis revealed strong absorbance in the UV. Moreover, the product reacted positively with iodine, chlorox spray, and the maleimide reactive reagent. These results indicate that the product is the desired heterobifunctional maleimide active ester crosslinker, maleimido-6- aminocaproyl-spacer-glutaryl ester of 1-hydroxy-2-nitrobenzene sulfonic acid, which has the structure:

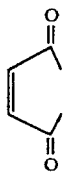 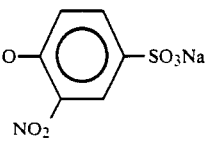

EXAMPLE II

Syntheiss of Immunotoxin Conjugates

The monoclonal antibody 260F9 was reacted with the heterobifunctional crosslinker, mal-sac-spacer-glut-HNSA as follows. 260F9 is a murine antifody, and is on deposit with the American Type Culture Collection (ATCC No. HB 8488), and recognizes a antigen found predominately on mammary tumor cells. 10 mg/ml of 260F9 was reacted with a two-fold molar excess of the thioether crosslinker in 0.1M sodium phosphate, pH 8, for about 25 minutes at room temperature. The progress of the reaction was followed by measuring the absorbance as described in Example I at 406 nm. At the end of 25 minutes the absorbance had increased to 0.57, and the derivatized antibody was separated from the reaction mixture by gel filtration using a Sephadex G-25 column (2.5×17 cm) in 40 mM sodium phosphate buffer, pH 6, containing 200 mM NaCL. This material was reacted, as described below, with the cytotoxin, recombinant ricin A chain.

Recombinant ricin A chain used to construct the conjugate is described in European Patent Application No. 84304801.8, inventors Lord et al., or in U.S. patent application Ser. No. 837,583. It was prepared for reaction with derivatized antibody by first reducing the molecule with 10 mM dithiothreotol, followed by removing excess reducing agent by gel filtration over a Sephadex G-25 column in 10 mM sodium phosphate, pH 7.5, containing 200 mM NaCl. Reduced recombianant ricin A chain was combined with derivatized antibody in a 1:2 molar ratio (antibody:recombinant ricin A chain). The solution was concentrated using an Amico stirred ultra filtration device to reduce the volume down to about 10 ml. The buffer employed was 40 mM sodium phoshate, pH 7.6, containing 200 mM NaCl. The reaction was allowed to proceed overnight at 4° C., and the sample was then chromatographed over a Sepharose S-300 column (2.2×80 cm) in 40 mM sodium phosphate, pH 6.5, containing 200 mM NaCl. This step removed any untreated recombinanat ricin A chain, as well as high molecular weight aggregates that are present in the reaction mixture.

Finally, the immunotoxin obtained in the preceding step was purified from any unreacted derivatized antibody by chromatographing the material obtained from the Sephacryl S-300 column over a phenyl sepharose column (1.8×19 cm). This mixture was applied to the column in 25 mM sodium phosphate, pH 6.5, containing 1 mM EDTA, and 1M NaCl. Immunotoxin and untreated antibody were eluted from the phenyl-sepharose column using a linear gradient consisting of 200 ml of the starting buffer, and 200 ml of 25 mM sodium phosphate, pH 6.5, containing 1 mM EDTA, and 50% propylene glycol. Fractions were collected and analyzed by sodium dodecyl sulfate polyacrylamide gel electrophoresis, to identify those fractions containing antibody or immunotoxin. Fractions that contained only immunotoxin were pooled and dialyzed against phosphate buffer saline, pH 6.5, containing 1 mM EDTA. The solution was concentrated on a YM-10 membrane in a stirred Amicon ultrafiltration device. It was determined that the immunotoxin composition consisted of 80% 1:1 recombinant ricin A:antibody; 8.5% 2:1 recombinant ricin A:antibody; 8% 3:1 recombinant ricin:antibody; and 3.8% 4:1 recombinant ricin A: antibody.

It will be appreciated by those skilled in the art that naturally occurring ricin, ricin A, or chemically treated ricin A chain, so as to modify carbohydrate structure on ricin A chain, can be substituted for recombinant ricin A chain. The procedures for making Mab conjugates with naturally occurring ricin are similar to those described above. Alternatively, the methods shown in U.S. Pat. No. 4,340,535 can be employed.

EXAMPLE III

Pharmokinetics

Experiments were done to characterize the in vivo life time of immunotoxin conjugates linked by the cross-linkers of the instant invention. The experiments were done using the recombinant ricin toxin A chain antibody conjugate produced as in Example II using the monoclonal antibody 454A12. The experiment was conducted by injecting an appropriate amount of immunotoxin wherein antibody and cytotoxin are linked by the linker shown in Example I, mal-sac-spacer-glut-HNSA. Immunotoxin was injected by a canula into a vein of 250 gram rats. Blood was removed from the rats at various time intervals and the concentration of intact immunotoxin was determined using a sandwich ELISA assay well known to those skilled in the art. The capture antibody was anti-rRA and the detection antibody was horseradish peroxidase-labeled anti-mouse IgG.

FIG. 1 shows that the clearance of immunotoxin from blood is biphasic, with a rapid, or alpha phase, and a slower second, or beta phase. The half-life for the immunotoxin in the alpha phase is about 3.2–3.7 hours. The beta phase half-life was considerably longer, and was about 24–29 hours. These results were compared with the pharmokinetics of immunotoxin conjugates wherein antibody and toxin are linked by a disulfide linkage. The linkage was formed with iminothiolane using technique well known in the art. It is apparent from FIG. 1 that the alpha phase is considerably shorter than that observed for immunotoxins having a thioether linkage, and is about 1.9 hours. Similarly, the beta phase for the disulfide linked immunotoxin is shorter, and is about 9.5 hours. LL refers to the crosslinker used in Example 1, or maleimido-6-aminocapryl-spacerglutaryl ester of 1-hydroxy-2-nitrobenzene sulfonic acid.

EXAMPLE IVE

Effect of Immunotoxin Conjugates On Protein Synthesis, and Mitochondrial Activity Experiments were done to determine the efficacy of immunotoxins linked by a thioether bond. Thus, immunotoxins produced as described in Example II were tested for their ability to inhibit protein synthesis, and mitochondrial reductase activity (MTT). The assays were conducted as described by Ramakrishnan, S., and Houston, L.L. (1984) in *Science,* 223, 58–61; and Bjorn, M. J., Ring, D., and Frankel, in *Cancer Res.,* 45, 1214–11221, respectively. Two immunotoxin conjugates were utilized, the first consisting of a monoclonal antibody 260F9 bound to recombinant ricin A chain, or monoclonal antibody 454A12 also bound to recombinant ricin A chain. 454A12 binds to the transferrin receptor and is on deposit with In Vitro International, 7885 Jackson Road, Suite 4, Ann Arbor, Mich., Accession No. 10075. The results were compared to immunotoxin conjugates having a disulfide linkage formed by iminothiolane. Table 1 shows that the disulfide linked immunotoxin conjugates are considerably more effective in both assay systems when compared to either of the immunotoxin conjugates linked by a thioether linkage. Nevertheless, it is important to note that the thioether linked immunotoxin conjugates are effective both in inhibiting protein synthesis, and in the MTT assay.

TABLE I

| | | TCID50 (nM) | | | |
|---|---|---|---|---|---|
| | | 260F9 | | 454A12 | |
| Linker | Site | Protein Synthesis | MTT | Protein Synthesis | MTT |
| IT-S-S | 259 | 0.01 | 0.02 | 0.006 | 0.002 |
| | | | 0.05 | | 0.008 |
| | | | 0.11 | | 0.014 |
| Thioether-S- | 259 | <1 | 2.5 | 6 | 0.06 |
| | | | 6.5 | | 0.9 |
| | | | 13.1 | | 9.0 |
| | 19 | 0.3 | 15 | 3 | 0.24 |
| | | | 8.5 | | 4.2 |
| | | | 9.4 | | 19.7 |

EXAMPLE V

Anti-Tumor Effects

The effectiveness of immunotoxin conjugates linked by a thioether bond against tumor cells was tested in a mouse model system. Tumorigenic OC21-OVCAR-3 cells [FitzGerald, D. J., Trowbridge, I. S., Pastan, I., and Willingham, M. D. (1983) Enhancement of toxicity in anti-transferrin receptor antibody-Pseudomonas exotoxin conjugates by adenovirus. Proc. Natl. Acad. Sci. U.S.A., 80, 4134–4136] were injected intraperitoneally into nude mice, and then groups of 39 mice treated with an immunotoxin conjugate at each of 4, 6 and 8 days subsequent to injection of the tumor cells. The immunotoxin conjugate consisted of the monoclonal antibody 454A12 linked torecombinant ricin A chain via the linker shown in Example I. For comparative purposes the same monoclonal antibody was linked to recombinant ricin A chain via iminothiolane.

Generally, control mice that were not treated with immunotoxin died between 27 and 35 days after being injected with OC21-OVCAR-3 cells with a median of 22.5 days. In contrast, at a 30 μg dose of 454A12-IT (iminothiolane) rRA the median survival was greater than 166 days. Similarly mice treated with the immunotoxin conjugate having the thioether linker also survived longer than control mice. At 30 μg 454A12-LL-rRA the median survival time was 47.8 days.

Thus, it is apparent that immunotoxin conjugates consisting of antibody and cytotoxin linked by a thioether linkage are efficacious against tumors.

Immunotoxin conjugates having a thioether linkage were further tested for their anti-cancer effects in a second animal model, the MX-1 tumor system. The MX-1 tumor model is described by A. A. Ovejera, et al., *Annal. of Clinical and Laboratory Science*, 8:51 (1978), and is hereby incorporated by reference.

The human breast tumor cell line, MX-1, was injected into nude mice, and tumor volume as a function of immunotoxin concentration measured at different time intervals. The experiment was done using immunotoxin conjugates consisting of monoclonal antibody 260F9 linked to recombinant ricin A chain via either a disulfide linkage formed by iminothiolane, or the thioether crosslinker shows in Example 1. The results are presented in FIG. 2. It is apparent that when compared to mice that were not treated with immunotoxin, that both immunotoxins were efficacious. For example, mice treated with the disulfide linked immunotoxin after 10 days at a dose of 7 μg had a tumor volume of less than 100 mm$^3$, whereas control mice exhibited a tumor volume of about 380 mm$^3$. Similar results in FIG. 3 were observed for the immunotoxin having a thioether linkage (LL) when it was administered at a dose of about 7-14 μg.

Having generally described the invention, it will be understood by those skilled in the art that there exist a wide range of equivalent materials and methods that can be substituted for those shown herein without affecting the spirit or scope of the invention. The scope of the invention should not be construed as being limited other than by the appended claims.

What is claimed is:

1. A method of killing cells, comprising contacting said cells with an immunotoxin consisting of at least one antibody and at least one cytotoxin linked by a thioether linkage by reaction with a linker comprising maleimido-6-aminocaproyl-spacer-glutaryl ester of 1-hydroxy-2-nitrobenzene.

2. A method as described in claim 1, wherein said antibody is selected from the group consisting of monoclonal, polyclonal or recombinant antibody, or fragments thereof.

3. A method as described in claim 2, wherein said cytotoxin is selected from the group consisting of ricin, diphtheria toxin, and abran, or fragments derived therefrom.

4. A method as described in claim 3, wherein said cytotoxin is ricin A chain.

5. A method for killing cells as described in claim 1, wherein said cells are tumor cells.

* * * * *